US009119666B2

(12) United States Patent
Kleyman et al.

(10) Patent No.: US 9,119,666 B2
(45) Date of Patent: Sep. 1, 2015

(54) ACCESS PORT WITH INTEGRATED FLEXIBLE SLEEVE

(75) Inventors: Gennady Kleyman, Brooklyn, NY (US); Anibal Rodrigues, Milford, CT (US)

(73) Assignee: Covidien LP, Mansfield, MA (US)

( * ) Notice: Subject to any disclaimer, the term of this patent is extended or adjusted under 35 U.S.C. 154(b) by 295 days.

(21) Appl. No.: 13/411,756

(22) Filed: Mar. 5, 2012

(65) Prior Publication Data

US 2012/0245430 A1 Sep. 27, 2012

Related U.S. Application Data

(60) Provisional application No. 61/467,428, filed on Mar. 25, 2011.

(51) Int. Cl.
*A61B 1/32* (2006.01)
*A61B 17/34* (2006.01)

(52) U.S. Cl.
CPC ..... *A61B 17/3423* (2013.01); *A61B 2017/3429* (2013.01); *A61B 2017/3435* (2013.01); *A61B 2017/3441* (2013.01); *A61B 2017/3443* (2013.01); *A61B 2017/3445* (2013.01); *A61B 2017/3466* (2013.01)

(58) Field of Classification Search
CPC ............... A61B 17/02; A61B 17/0218; A61B 17/0281; A61B 17/32; A61B 1/32; A61B 17/3421; A61B 17/3423; A61B 17/3462; A61B 2017/3429; A61B 2017/3435; A61B 2017/3441; A61B 2017/3443; A61B 2017/3445; A61B 2017/3447; A61B 2017/3466
USPC ......................................... 600/201–210, 215
See application file for complete search history.

(56) References Cited

U.S. PATENT DOCUMENTS

| | | | |
|---|---|---|---|
| 5,524,644 | A | 6/1996 | Crook |
| 5,803,921 | A | 9/1998 | Bonadio |
| 5,906,577 | A | 5/1999 | Beane et al. |
| 6,033,426 | A | 3/2000 | Kaji |
| 6,033,428 | A | 3/2000 | Sardella |
| 6,142,936 | A | 11/2000 | Beane et al. |
| 6,254,534 | B1 | 7/2001 | Butler et al. |
| 6,440,063 | B1 | 8/2002 | Beane et al. |
| 6,578,577 | B2 | 6/2003 | Bonadio et al. |

(Continued)

FOREIGN PATENT DOCUMENTS

| | | |
|---|---|---|
| EP | 1312318 | 12/2005 |
| EP | 2044897 | 4/2009 |

(Continued)

OTHER PUBLICATIONS

U.S. Appl. No. 13/091,246, filed Apr. 21, 2011, Paul D. Richard.

(Continued)

*Primary Examiner* — Christian Sevilla
*Assistant Examiner* — Eric S Gibson

(57) ABSTRACT

A surgical apparatus for positioning within a tissue tract accessing an underlying body cavity is adapted to tissues having different thicknesses. The surgical apparatus includes an anchor member and a flexible sleeve integrated with the anchor member. The anchor member defines at least one longitudinal port for reception of a surgical instrument. The surgical apparatus defines an adjustable length to accommodate tissues with different thicknesses.

20 Claims, 4 Drawing Sheets

"D2"
"D1"
112c
113
112a
112b
112
115
112d
111c
110
114
111
105
108
"H1"
"T"
"H4"
107
121
130
122
120

(56) References Cited

U.S. PATENT DOCUMENTS 6,582,364 B2 6/2003 Butler et al.
6,613,952 B2 9/2003 Rambo
6,623,426 B2 9/2003 Bonadio et al.
6,723,044 B2 4/2004 Pulford et al.
6,814,078 B2 * 11/2004 Crook .......................... 128/849
6,846,287 B2 1/2005 Bonadio et al.
6,958,037 B2 10/2005 Ewers et al.
7,008,377 B2 3/2006 Beane et al.
7,033,319 B2 4/2006 Pulford et al.
7,052,454 B2 5/2006 Taylor
7,081,089 B2 7/2006 Bonadio et al.
7,195,590 B2 3/2007 Butler et al.
7,300,399 B2 11/2007 Bonadio et al.
7,377,898 B2 5/2008 Ewers et al.
7,393,322 B2 7/2008 Wenchell
7,445,597 B2 11/2008 Butler et al.
7,537,564 B2 5/2009 Bonadio et al.
7,540,839 B2 6/2009 Butler et al.
7,559,893 B2 7/2009 Bonadio et al.
7,650,887 B2 1/2010 Nguyen et al.
7,704,207 B2 4/2010 Albrecht et al.
7,727,146 B2 6/2010 Albrecht et al.
7,766,824 B2 8/2010 Jensen et al.
7,815,567 B2 10/2010 Albrecht et al.
7,998,068 B2 8/2011 Bonadio et al.
8,226,553 B2 * 7/2012 Shelton et al. ................ 600/208
8,231,527 B2 * 7/2012 Beckman et al. ............. 600/208
2001/0037053 A1 11/2001 Bonadio et al.
2002/0183594 A1 12/2002 Beane et al.
2003/0187376 A1 10/2003 Rambo
2004/0092795 A1 5/2004 Bonadio et al.
2006/0161049 A1 7/2006 Beane et al.
2006/0161050 A1 7/2006 Butler et al.
2006/0247498 A1 11/2006 Bonadio et al.
2006/0247500 A1 11/2006 Voegele et al.
2007/0093695 A1 4/2007 Bonadio et al.
2007/0151566 A1 7/2007 Kahle et al.
2007/0203398 A1 8/2007 Bonadio et al.
2008/0200767 A1 8/2008 Ewers et al.
2008/0281161 A1 11/2008 Albrecht et al.
2009/0093850 A1 * 4/2009 Richard ........................ 606/300
2009/0187079 A1 7/2009 Albrecht et al.
2009/0292176 A1 * 11/2009 Bonadio et al. ............... 600/203
2009/0326332 A1 12/2009 Carter
2010/0063362 A1 * 3/2010 Bonadio et al. ............... 600/203
2010/0081995 A1 * 4/2010 Widenhouse et al. ... 604/164.08
2010/0094227 A1 4/2010 Albrecht et al.
2010/0249516 A1 * 9/2010 Shelton et al. ................ 600/203
2010/0312064 A1 * 12/2010 Weisenburgh et al. ....... 600/206
2011/0082341 A1 * 4/2011 Kleyman et al. .............. 600/206
2011/0201893 A1 * 8/2011 O'Prey et al. ................. 600/208
2012/0245430 A1 * 9/2012 Kleyman et al. .............. 600/208
2013/0066156 A1 * 3/2013 Seo .............................. 600/204

FOREIGN PATENT DOCUMENTS

WO WO 01/08581 2/2001
WO WO01/08581 2/2001
WO WO2004/054456 7/2004
WO WO 2004/054456 7/2004
WO WO 2004054456 A1 * 7/2004
WO WO 2004/075741 9/2004
WO WO2004/075741 9/2004
WO WO 2010/141409 12/2010

OTHER PUBLICATIONS

U.S. Appl. No. 13/030,164, filed Feb. 18, 2011, Gennady Kleyman.
U.S. Appl. No. 13/030,172, filed Feb. 18, 2011, Gennady Kleyman.
U.S. Appl. No. 13/030,178, filed Feb. 18, 2011, Gennady Kleyman.
U.S. Appl. No. 13/031,346, filed Feb. 21, 2011, Gennady Kleyman.
U.S. Appl. No. 13/031,352, filed Feb. 21, 2011, Gennady Kleyman.
U.S. Appl. No. 13/193,647, filed Jul. 29, 2011, Russell Pribanic.
U.S. Appl. No. 13/217,717, filed Aug. 25, 2011, Joshua Stopek.
U.S. Appl. No. 13/221,062, filed Aug. 30, 2011, Gregory Okoniewski.
U.S. Appl. No. 13/223,029, filed Sep. 1, 2011, Michael Davis.
U.S. Appl. No. 13/223,330, filed Sep. 1, 2011, Gregory Okoniewski.
U.S. Appl. No. 13/223,336, filed Sep. 1, 2011, Michael Davis.
U.S. Appl. No. 13/223,613, filed Sep. 1, 2011, Greg Fischvogt.
U.S. Appl. No. 13/223,627, filed Sep. 1, 2011, Gregory Okoniewski.
U.S. Appl. No. 13/223,645, filed Sep. 1, 2011, Gennady Kleyman.
U.S. Appl. No. 13/223,659, filed Sep. 2, 2011, Francesco Alfieri.
U.S. Appl. No. 13/223,678, filed Sep. 1, 2011, Gregory Okoniewski.
U.S. Appl. No. 13/223,700, filed Sep. 1, 2011, Gennady Kleyman.
U.S. Appl. No. 13/224,353, filed Sep. 2, 2011, Gennady Kleyman.
U.S. Appl. No. 13/224,354, filed Sep. 2, 2011, Greg Okoniewski.
U.S. Appl. No. 13/224,355, filed Sep. 2, 2011, Anibal Rodrigues Jr.
U.S. Appl. No. 13/224,358, filed Sep. 2, 2011, Andrew Barnes.
U.S. Appl. No. 13/228,937, filed Sep. 9, 2011, Dino Kasvikis.
U.S. Appl. No. 13/228,960, filed Sep. 9, 2011, Russell Pribanic.
European Search Report EP08253236 dated Feb. 10, 2009.
European Search Report EP09251613 dated Mar. 24, 2011.
European Search Report EP10250526 dated Jun. 23, 2010.
European Search Report EP10250638 dated Jul. 19, 2010.
European Search Report EP10250643 dated Jun. 23, 2010.
European Search Report EP10250881 dated Aug. 18, 2010.
European Search Report EP10250885 dated Aug. 18, 2010.
European Search Report EP10250944 dated Jul. 29, 2010.
European Search Report EP10251218 dated Jun. 15, 2011.
European Search Report EP10251317 dated Oct. 15, 2011.
European Search Report EP10251359 dated Nov. 8, 2010.
European Search Report EP10251399 dated Sep. 13, 2010.
European Search Report EP10251486 dated Oct. 19, 2010.
European Search Report EP10251693 dated Feb. 3, 2011.
European Search Report EP10251718 dated Jan. 28, 2011.
European Search Report EP10251751 dated Apr. 28, 2011.
European Search Report EP10251796 dated Jan. 31, 2011.
European Search Report EP10251955 dated Feb. 21, 2011.
European Search Report EP10251983 dated Feb. 15, 2011.
European Search Report EP10251984 dated Feb. 10, 2011.
European Search Report EP10251985 dated Feb. 15, 2011.
European Search Report EP10251986 dated Mar. 7, 2011.
European Search Report EP12160930.9 dated Jun. 5, 2012.

* cited by examiner

ACCESS PORT WITH INTEGRATED FLEXIBLE SLEEVE

CROSS REFERENCE TO RELATED APPLICATION

The present application claims the benefit of and priority to U.S. Provisional Application Ser. No. 61/467,428, filed on Mar. 25, 2011, the entire contents of which are incorporated herein by reference.

BACKGROUND

1. Technical Field

The present disclosure relates generally to surgical apparatuses for use in minimally invasive surgical procedures, such as endoscopic and/or laparoscopic procedures, and more particularly, relates to a surgical apparatus that allows multiple surgical instruments to be inserted through a single incision.

2. Description of Related Art

Today, many surgical procedures are performed through small incisions in the skin, as compared to large incisions that are typically required in traditional procedures, in an effort to reduce trauma to the patient and reduce the patient's recovery time. Generally, such procedures are referred to as "endoscopic", unless performed on the patient's abdomen, in which case the procedure is referred to as "laparoscopic." Throughout the present disclosure, the term "minimally invasive" should be understood to encompass both endoscopic and laparoscopic procedures.

During a typical minimally invasive procedure, surgical objects, such as endoscopes, graspers, staplers and forceps, are inserted into the patient's body through the incision in tissue. In general, prior to the introduction of the surgical object into the patient's body, insufflation gas is supplied to the target surgical site to enlarge its surrounding area and create a larger, more accessible work area. This is accomplished with a substantially fluid-tight seal that maintains the insufflation gas at a pressure sufficient to inflate the target surgical site.

Different patients or different target surgical sites have different tissue thicknesses. For that reason, it is desirable to have the substantially fluid-tight seal adaptable to accommodate different tissue thicknesses. It is also desirable to insert instrumentation at the target surgical site while maintaining the pressure of the insufflation gas by using the substantially fluid-tight seal. Further, it is desirable to increase ease of use or increase maneuverability of multiple instruments simultaneously operated through the substantially fluid-tight seal.

The existing access devices in the prior art such as wound retractors may accomplish one objective addressed above but fails to meet all the other objectives. For instance, wound retractors are generally known for permitting operation of multiple instruments therethrough, but are also known for their drawbacks such as failure to prevent escape of insufflation gas, difficult placement and cumbersome use.

Based on the above, a continuing need exists for an access device to provide greater freedom of movement of surgical instruments, with enhanced sealing and retraction features, and with increased flexibility to accommodate tissues of different thicknesses.

SUMMARY

Disclosed herein is a surgical apparatus for positioning within a tissue tract accessing an underlying body cavity. The surgical apparatus includes an anchor member that defines at least one longitudinal port for reception of object, and further has a flexible sleeve attached to the anchor member. The surgical apparatus defines an adjustable insertion length.

In one embodiment, the flexible sleeve includes a sheath in a generally cylindrical configuration with an adjustable length. The flexible sleeve may include a ring member attached to the sheath, where the ring member is adapted to roll upon the sheath to transition the flexible sleeve from a first length to a second length. The sheath defines an unrolled state that corresponds to a first length of the flexible sleeve and a rolled state that corresponds to a second length of the flexible sleeve, and the first length is different from the second length.

In a preferred embodiment, the ring member defines a hole for reception of a suture therethrough.

In a certain embodiment, the surgical apparatus has a suture to maintain the surgical apparatus at its desired insertion length.

In another embodiment, the flexible sleeve is attached to the anchor member by glue, suture or an overmolding process.

DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
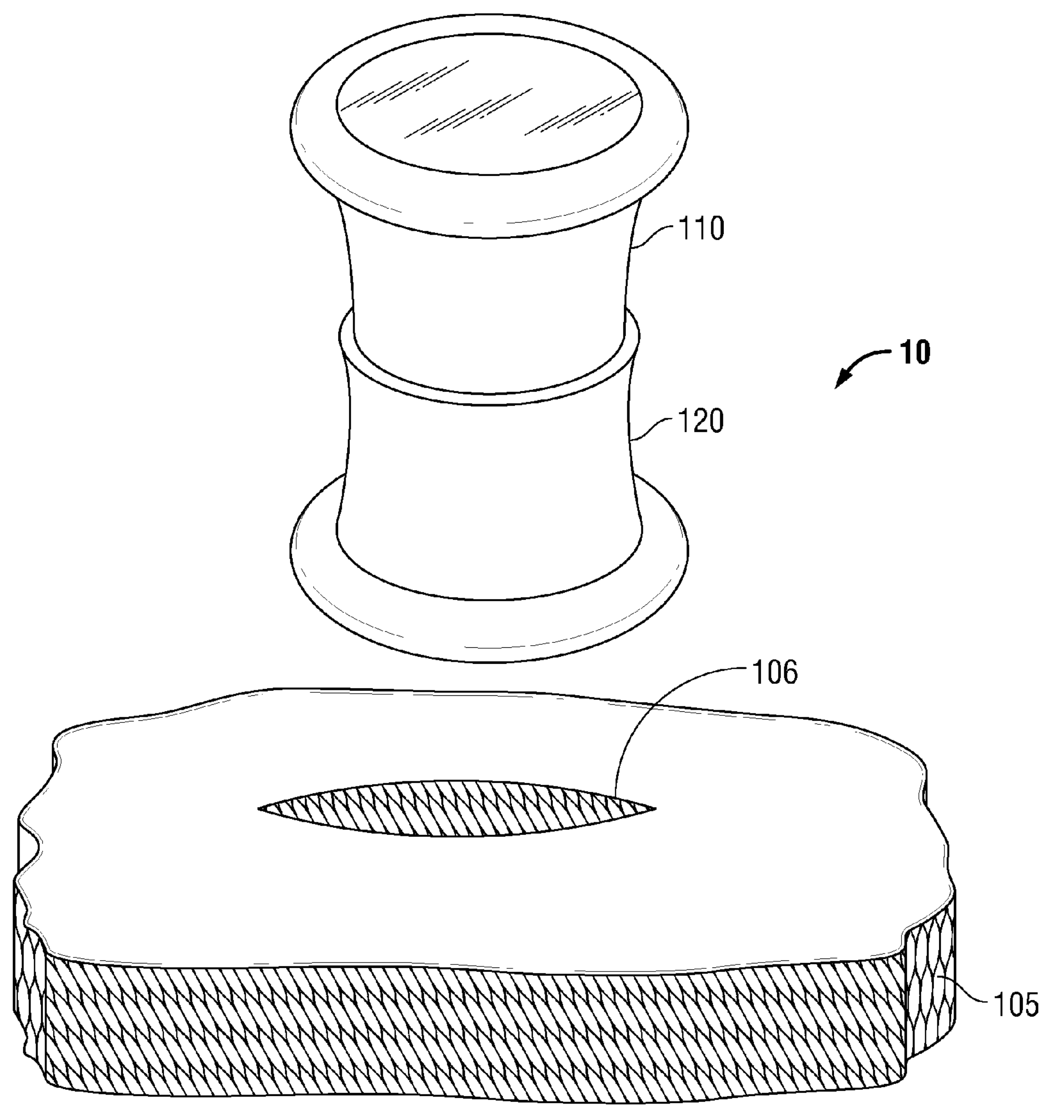
FIG. 1 is a front perspective view of a surgical apparatus in accordance with the principles of the present disclosure illustrating a surgical apparatus positioned relative to the tissue.

Particular embodiments of the present disclosure will be described herein with reference to the accompanying drawings. As shown in the drawings and as described throughout the following description, and as is traditional when referring to relative positioning on an object, the term "proximal" or "trailing" refers to the end of the apparatus that is closer to the user and the term "distal" or "leading" refers to the end of the apparatus that is farther from the user. In the following description, well-known functions or constructions are not described in detail to avoid obscuring the present disclosure in unnecessary detail.

One type of minimal invasive surgery described herein employs a device that facilitates multiple instrument access through a single incision. This is a minimally invasive surgical procedure, which permits a user to operate through a single entry point, typically the patient's navel. Additionally, the presently disclosed device may be used in a procedure where a naturally occurring orifice (e.g. vagina or anus) is the point of entry to the surgical site. The disclosed procedure involves insufflating the body cavity and positioning a portal member within, e.g., the navel of the patient. Instruments including an endoscope and additional instruments such as graspers, staplers, forceps or the like may be introduced within a portal member to carry out the surgical procedure. An example of such a surgical portal is disclosed in U.S. patent application Ser. No. 12/244,024, Pub. No. U.S. 2009/0093752 A1, filed Oct. 2, 2008, the entire contents of which are hereby incorporated by reference herein.

Referring now to the drawings, in which like reference numerals identify identical or substantially similar parts throughout the several views, FIG. 1 illustrates a surgical apparatus 10 in accordance with the principles of the present disclosure. The surgical apparatus 10 is adapted for insertion in a tissue opening 106 within a tissue tract 105, e.g., through the abdominal or peritoneal lining in connection with a laparoscopic surgical procedure. The surgical apparatus 10 will be described in greater detail hereinbelow.

As shown in FIG. 1, the surgical apparatus 10 may define a substantially hourglass shape. However, it is contemplated that the surgical apparatus 10 may define other configurations both prior and subsequent to insertion within the tissue tract 105.

Figure 2:
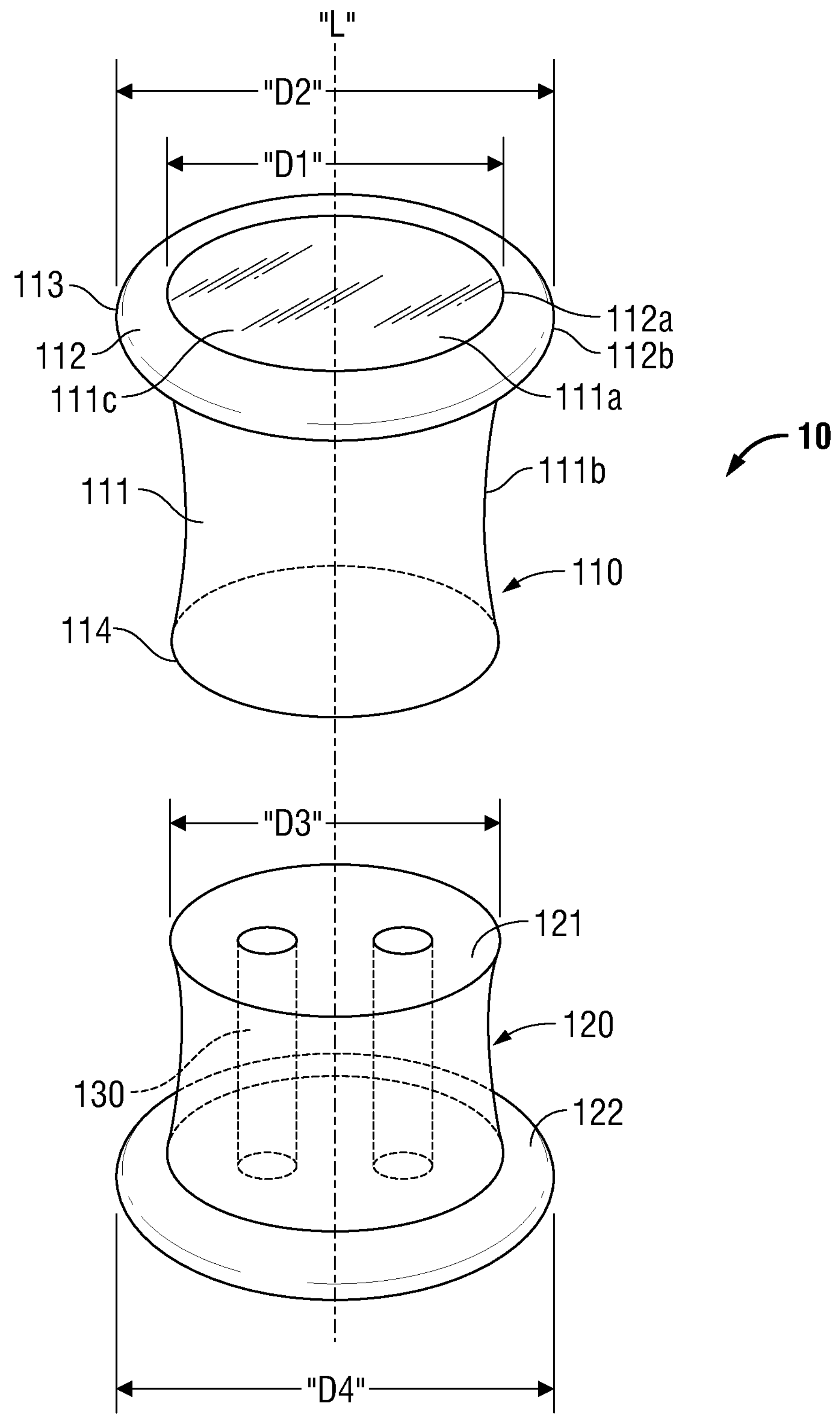
FIG. 2 is an exploded view of the surgical apparatus of FIG. 1 illustrating a sheath and an anchor member.

With reference to FIG. 2, the surgical apparatus 10 defines a longitudinal axis "L", and includes a proximal portion (or a flexible sleeve) 110 and a distal portion (or an anchor member) 120 which are axially aligned along the longitudinal axis "L," with the proximal portion 110 mounted on top of or mounted proximally with respect to the distal portion 120. The proximal portion 110 includes a sheath or a liner 111 which, in one embodiment, exhibits a generally cylindrical configuration. It is envisioned that the sheath 111 may exhibit other configurations. The sheath 111 is disposed between a proximal end 113 and a distal end 114 of the proximal portion 110. The sheath 111 defines an inner surface 111*a* and an outer surface 111*b*. The inner surface 111*a* defines a longitudinal passage 111*c* therein having a diameter of "D1" in its radial dimension. In one embodiment, the radial dimension, "D1", is uniform along the length of the sheath 111. It is envisioned that the entire length of the sheath 111 is insertable into the tissue opening 106.

Figure 3:
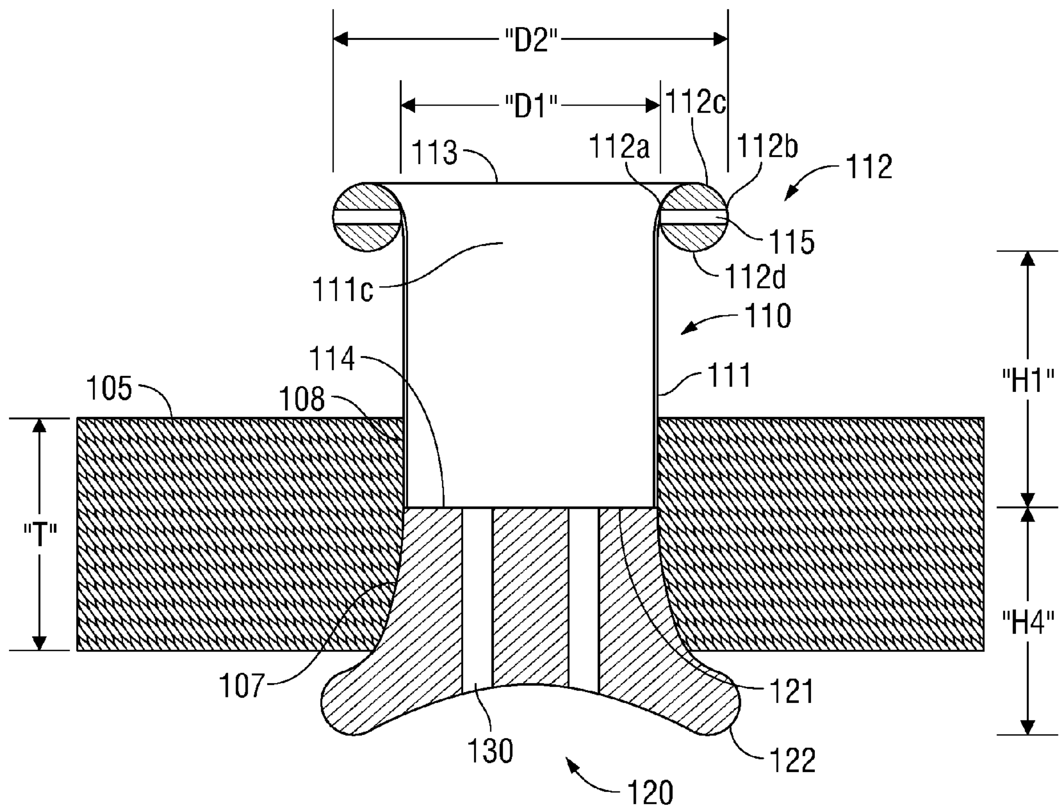
FIG. 3 is a side cross-sectional view of the surgical apparatus of FIG. 1 illustrating the sheath in an unrolled state.
Figure 4:
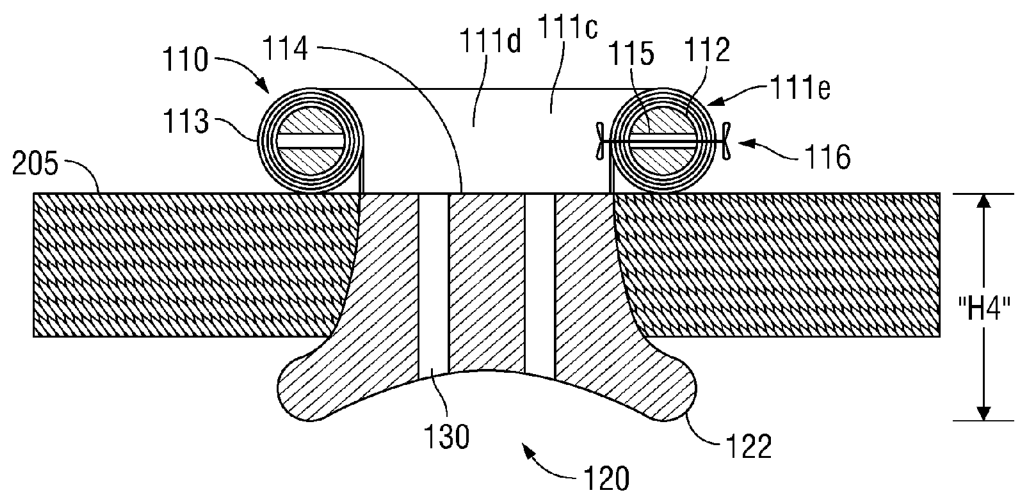
FIG. 4 is a side cross-sectional view of the surgical apparatus of FIG. 1 illustrating the sheath in a fully rolled state.
Figure 5:
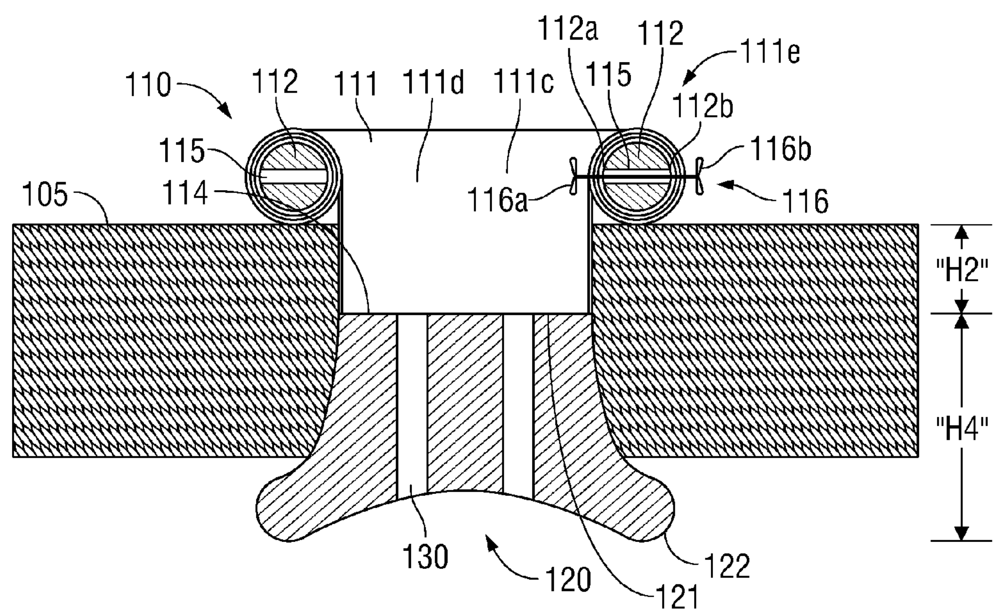
FIG. 5 is a side cross-sectional view of the surgical apparatus of FIG. 1 illustrating the sheath in a half-way rolled state.

With additional reference to FIG. 3, the proximal portion 110 further includes a ring member 112 mounted at its proximal end 113 in connection with the sheath 111. The ring member 112 includes an inner wall 112*a*, an outer wall 112*b*, a proximal surface 112*c* and a distal surface 112*d*. The ring member 112 further includes two or more holes 115, as illustrated in FIG. 3, which are disposed at the circumference of the ring member 112. Each hole 115 is a hollow passage communicating between the inner wall 112*a* and the outer wall 112*b*. The inner wall 112*a* defines an inner diameter which is identical to the diameter "D1" of the longitudinal passage 111*c*. The ring member 112 is configured to be disposed exteriorly of the tissue opening 106. Specifically, the outer wall 112*b* is configured to have an outer diameter "D2," which is larger than "D1" and also significantly greater than the size of the tissue opening 106. Due to its large dimension, the outer wall 112*b* inhibits the ring member 112 from entering the tissue opening 106 and also facilitates retraction of the tissue opening 106, as illustrated in FIGS. 4 and 5.

The ring member 112 is configured to roll along the longitudinal length of the sheath 111, causing the sheath 111 to be wrapped about the ring member 112, and also causing the sheath 111 to be rolled upon itself. As the ring member 112 rolls along the sheath 111 in a distal direction, the sheath 111 transitions from an unrolled or first state as illustrated in FIG. 3 to a fully rolled or second state as illustrated in FIG. 4.

The proximal portion 110 defines an insertion length, which represents the length of the proximal portion 110 that can be inserted into the tissue opening 106. The insertion length is a distance measured from the distal end 114 of the proximal portion 110 to the distal edge 112*d* of the ring member 112. The insertion length varies depending on the rolling state of the sheath 111. When the sheath 111 is unrolled, as illustrated in FIG. 3, the proximal portion 110 has a maximum insertion length of "H1." When the sheath 111 is rolled upon itself to an extent that the proximal end 113 meets the distal end 114, as illustrated in FIG. 4, the proximal portion 110 has a minimum insertion length. Therefore, as the ring member 112 rolls along the sheath 111 in a distal direction, the insertion length of the sheath 111 transitions between a maximum value to a minimum value. FIG. 5 illustrates when the sheath 111 is rolled halfway, the proximal portion 110 has an insertion length of "H2" which is less than the maximum insertion length but greater than the minimum insertion length.

It is envisioned that a suture 116 may be used to secure the proximal portion 110 at its desired insertion length by specifically securing the rolled portion 11 le of the sheath 111. For instance, as illustrated in FIG. 5, the suture 116 connects the rolled portion 111*e* of the sheath 111 to the unrolled portion 111*d* of the sheath 111 through the hole 115 of the ring member 112. The suture 116 has one end 116*a* extending beyond the inner wall 112*a* of the ring member 112 and secured with respect to the unrolled portion 111 d of the sheath 111, and has the other end 116*b* extending beyond the outer wall 112*b* of the ring member 112 and secured with respect to the rolled portion 111*e* of the sheath 111.

Suture 116 represents one exemplary means of selecting, securing and maintaining a desired rolled state of the sheath 111 for purposes of maintaining a desired insertion length of the proximal portion 110. Other fastening means are also envisioned, including clips, snaps, or hooks for holding the sheath 111 at a desired rolled state. In addition, the rolled state of the sheath 111 may be facilitated and/or maintained by the ring member 112 having a cross-sectional shape that is non-circular, such as a crescent-shaped cross-section or the like.

The distal portion 120 of the surgical apparatus 10, as illustrated in FIG. 2, defines a proximal end 121 and a distal end 122. The proximal end 121 defines a diameter "D 3" which is greater than or equal to the diameter "D1" of the proximal portion 110. The distal end 122 defines a diameter "D4" which is substantially greater than "D3" for anchoring the surgical apparatus interiorly with respect to the tissue tract 105. In one embodiment, the distal end 122 defines a concave configuration, as illustrated in FIG. 3.

The distal portion 120 defines an insertion length "H4" which is the minimum length required to anchor the surgical apparatus 10 within any type of tissue 105. The insertion length "H4" of the distal portion 120 is constant. As the proximal portion 110 is mounted on top of the distal portion 120, the sum of the insertion lengths of the proximal portion 110 and the distal portion 120 corresponds to the insertion length of the entire surgical apparatus 10, which represents the length of the surgical apparatus 10 that can be inserted into the tissue tract 105. Since the insertion length of the distal portion 120 is constant, and since the insertion length of the proximal portion 110 varies depending on the rolling state of the sheath 111, the insertion length of the entire surgical apparatus 10 changes dynamically due to the rolling of the sheath 111. Similar to the insertion length of the proximal portion 110, the insertion length of the surgical apparatus 10 is at maximum when the sheath 111 is unrolled, as illustrated in FIG. 3. The insertion length of the surgical apparatus 10 is at minimum when the sheath is rolled to a maximum degree, as illustrated in FIG. 4.

The insertion length of the surgical apparatus 10 can be adjusted to accommodate tissue tracts 105 of different thickness. In a situation when the maximum insertion length of the surgical apparatus 10 readily fits in the tissue tract 105, the sheath 111 needs not be rolled upon. However, in situations in which the tissue tract 105 has a thickness "T", as illustrated in FIG. 3, that is less than the maximum insertion length of the surgical apparatus 10, the ring member 112 may roll distally along the length of the sheath 111 to approximate the tissue tract 105, causing the insertion length of the surgical apparatus 10 to approximate the thickness "T" of the tissue tract 105, as illustrated in FIG. 5.

The distal portion 120 further includes at least one longitudinal port 130 extending between the proximal end 121 and the distal end 122 along the longitudinal axis "L." Each longitudinal port 130 receives one surgical instrument.

In a preferred embodiment, a plurality of ports 130 is disposed within the distal portion 120. The longitudinal ports 130 are configured symmetrically with respect to the longitudinal axis "L". The ports 130 are spaced equidistant from the longitudinal axis "L". Each port 130 may be spaced equidistant from its neighboring ports. Each port 130 is dimensioned to receive a surgical object, e.g. a surgical instrument (not shown) therethrough. Upon introduction of a surgical object (not shown) through a port 130, the port 130 establishes and maintains a substantial sealed relation about the surgical object.

In a certain embodiment, at least one of the ports 130 includes an integrated flexible cannula therein, obviating the need of disposing a separate cannula therein for purposes of sealingly engaging instruments such as endoscope, graspers and staplers.

The ring member 112 may be made of a rigid or semi rigid material such as plastic or rubber, but preferably is formed from a material that is rigid enough to maintain a generally circular configuration when in use while at the same time being flexible enough so as to enable a user to roll in around itself. The distal portion 120 may be made from a semi-resilient, disposable, compressible and flexible type (e.g. rubber or sponge) material, for example, but not limited to, a suitable foam, gel material, or soft rubber having sufficient compliance to form a seal about one or more surgical objects, and also establish a sealing relation with the tissue tract 105 and with the surgical object. In one embodiment, the foam includes a polyisoprene material. The resilient nature of the distal portion 120 provides an easy insertion and removal of the surgical apparatus 10 through the tissue 105. The sheath 111 is made of a material that is also able to establish a sealing relation with the tissue tract 105.

In one embodiment, the proximal portion 110 is an integrated part of the distal portion 120. The proximal portion 110 and the distal portion 120 are formed in one piece. Alternatively, the proximal portion 110 is permanently attached to the distal portion 120 of the surgical apparatus by glue, suture or by an overmolding process.

In another embodiment, the proximal portion 110 is detachably connected to the distal portion 120 of the surgical apparatus 10.

In operation, before insertion of the surgical apparatus 10 into the tissue tract 105, the surgeon first unrolls the sheath 111 to its unrolled state by rolling the ring member 112 in a proximal direction along the length of the sheath 111. Second, the surgeon introduces the distal portion 120 of the surgical apparatus 10 into the tissue tract 105 through the tissue opening 106 and positions the distal portion 120 in a manner such that the distal end 122 abuts the underside of the tissue tract 105 as illustrated in FIG. 3. The distal portion 120 forms a sealing relation with the tissue tract 105 that is in contact therewith, i.e., tissue 107 in FIG. 3. Third, while the distal portion 120 is anchored interiorly with respect to the tissue tract 105, the surgeon slightly pulls the sheath 111 in a proximal direction so that the sheath 111 is fully unfurled and forms a sealing relation with the tissue tract 105 that is in contact therewith, i.e., tissue 108 as seen in FIG. 3. However, if the distal portion 120 by itself fully accommodates the tissue thickness, as seen in FIG. 4, the surgeon may skip the third step and proceeds directly to the fourth step. At the fourth step, the surgeon rolls the ring member 112 in a distal direction along length of the sheath 111 to create tension in the sheath 111 thereby retracting the tissue opening 106. The same rolling step also causes to the ring member 112 to approach the upper side of the tissue tract 105, which, in turn, reduces the insertion length of the surgical apparatus 10 to approximate the thickness "T" of the tissue tract 105. Finally, the surgeon uses suture 116 or another fastening mechanism to secure the rolled portion 111*e* of the sheath 111 in order to maintain the surgical apparatus 10 at its desired insertion length.

In use, the proximal portion 110 with its relatively wide open space 111*c* above the plurality of ports 130, as defined by the sheath 111, provides the surgeon a large free space to manipulate portions of the surgical instruments positioned above the ports 130, ultimately resulting in a significantly increased range of motion of the surgical instruments inserted through the surgical apparatus 10 and also facilitating off-axis motions of the surgical instruments. Further, the configuration of the proximal portion 110 by employing a sheath 111 increases the flexibility of the surgical apparatus 10 such that the overall shape of the surgical apparatus 10 can be easily manipulated to facilitate its insertion through the tissue opening 106. Since the surgical apparatus 10 can be easily reduced to a small dimension by collapsing the sheath 111, a large incision opening is no longer necessary for permitting entry of the surgical apparatus 10. Therefore, the size of the incision can be considerably reduced as well, ultimately reducing trauma experienced the patient during creation of the incision, as well as reducing the patient's recovery time.

It should also be recognized that, while the surgical apparatus 10 is shown in use having the distal portion 110 located within the incision, it is envisioned that the device may also be used with the distal portion 110 being positioned entirely below the incision, allowing the rolling of the sheath 111 to retract the incision. Also, it should also be recognized that, while the surgical apparatus 10 is shown in use having the sheath 111 disposed proximally relative to the distal portion 110, it is envisioned that the device may also be used in the opposite fashion, e.g., with the ring member 112 inserted through the incision, e.g., pre-rolled by a user prior to it being inserted through the incision, and with the compressible material positioned above the incision, again allowing the rolling of the sheath 111 to retract the incision.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Different embodiments of the disclosure may be combined with one another based on the particular needs of the patients to achieve optimal results of the surgical procedures. Those skilled in the art will envision other modifications within the scope and spirit of the claims appended hereto.

What is claimed is:

1. A surgical apparatus for positioning within a tissue tract accessing an underlying body cavity, which comprises:

an anchor member including at least one longitudinal port defining a passage for reception of a surgical instrument in a sealing relation, the at least one longitudinal port defining a first diameter; and a flexible sleeve permanently attached to a proximal end portion of the anchor member, the flexible sleeve including a ring member attached to the flexible sleeve, the ring member adapted to be rolled such that the flexible sleeve may be rolled around the ring member to thereby transition the flexible sleeve from a first length to a second length so as to position the anchor member within the tissue tract, the flexible sleeve defining a longitudinal passage having a second diameter larger than the first diameter of the at least one longitudinal port.

2. The surgical apparatus according to claim 1, wherein the surgical apparatus defines an adjustable insertion length corresponding to tissue tracts of different thicknesses.

3. The surgical apparatus according to claim 1, wherein the flexible sleeve includes a sheath in a generally cylindrical configuration.

4. The surgical apparatus according to claim 3, wherein the ring member has a non-circular cross-sectional shape that maintains the sheath in a rolled position and helps prevent the sheath from unrolling.

5. The surgical apparatus according to claim 4, wherein the ring member is adapted for disposition exteriorly of the tissue tract.

6. The surgical apparatus according to claim 3, wherein the sheath defines an unrolled state that corresponds to the first length of the flexible sleeve and a rolled state that corresponds to the second length of the flexible sleeve, the first length is different from the second length.

7. The surgical apparatus according to claim 1, wherein the flexible sleeve is attached to the anchor member by glue, suture or an overmolding process.

8. The surgical apparatus according to claim 1, wherein the anchor member is adapted for disposition interiorly of the tissue tract.

9. The surgical apparatus according to claim 1, wherein the anchor member further includes a second longitudinal port.

10. A surgical apparatus defining a longitudinal axis for positioning within a tissue tract accessing an underlying body cavity, which comprises:

a foam anchor member defining a proximal end, a distal end, and including at least one longitudinal port defining a passage extending between the proximal and distal ends and being configured for reception of a surgical object in a sealing relation, the at least one longitudinal port including a first diameter; and a sheath having a distal end and a proximal end, the distal end of the sheath attached to the proximal end of the foam anchor member, the sheath having a rollable ring attached at the proximal end thereof, the rolling of the sheath retracting an incision such that the foam anchor member is positioned below the incision, the sheath defining a longitudinal passage having a second diameter larger than the first diameter of the at least one longitudinal port.

11. The surgical apparatus according to claim 10, wherein the sheath is configured to roll upon itself along the longitudinal axis.

12. The surgical apparatus according to claim 10, wherein the surgical apparatus defines an adjustable length.

13. The surgical apparatus according to claim 12, wherein the sheath defines an unrolled state that corresponds to a first length of the surgical apparatus and a rolled state that corresponds to a second length of the surgical apparatus, the first length is different from the second length.

14. The surgical apparatus according to claim 13, wherein the rollable ring has a non-circular cross-sectional shape so as to prevent the sheath from transitioning from the rolled state towards the unrolled state.

15. The surgical apparatus according to claim 14, wherein the rollable ring defines a hole for receiving a suture therethrough.

16. The surgical apparatus according to claim 13, wherein the surgical apparatus further comprises a suture to secure the sheath in the rolled state.

17. The surgical apparatus according to claim 10, wherein the sheath defines a generally cylindrical configuration.

18. The surgical apparatus according to claim 10, wherein the surgical apparatus exhibits an hourglass configuration.

19. The surgical apparatus according to claim 10, wherein the foam anchor member is made of a sponge or rubber like material.

20. The surgical apparatus according to claim 10, wherein the sheath is attached to the foam anchor member by glue, suture or an overmolding process.

* * * * *